United States Patent [19]

Calogero

[11] Patent Number: 4,969,898
[45] Date of Patent: Nov. 13, 1990

[54] EXPANDABLE PROSTHESIS FOR CORRECTING MYODYSTROPHIES

[76] Inventor: Marianna Calogero, Via Sulmona No. 23, Milano, Italy

[21] Appl. No.: 383,584

[22] Filed: Jul. 24, 1989

[30] Foreign Application Priority Data

Aug. 8, 1988 [IT] Italy .............................. 21725/88[U]

[51] Int. Cl.⁵ .............................................. A61F 2/12
[52] U.S. Cl. ............................................ 623/8; 623/7
[58] Field of Search ........................................ 623/8, 7

[56] References Cited

U.S. PATENT DOCUMENTS

| | | | |
|---|---|---|---|
| 3,852,833 | 12/1974 | Köneke et al. .......................... | 623/7 |
| 4,263,682 | 4/1981 | Bejarano .................................. | 623/8 |
| 4,433,440 | 2/1984 | Cohen ...................................... | 623/8 |
| 4,605,412 | 8/1986 | LaForest et al. ........................ | 623/8 |
| 4,643,733 | 2/1987 | Becker ..................................... | 623/8 |
| 4,769,036 | 9/1988 | Modir ...................................... | 623/8 |

OTHER PUBLICATIONS

Dobbins, B., "Instant Calves", Muscle and Fitness, Dec. 1986.

*Primary Examiner*—Randall L. Green
*Assistant Examiner*—Stephanie L. Iantorno
*Attorney, Agent, or Firm*—Beveridge, DeGrandi & Weilacher

[57] ABSTRACT

Prosthesis for the correction of myodystrophies; the prosthesis comprises a shaped body in an elastomeric material, having the form and consistency of the tissues of the area of the limb to be corrected. The body of the prosthesis has at least one elastically dilatable part defining a cavity which can be expanded by filling with a pressurized liquid; a filling tube is connected to said expandable cavity by a check valve.

12 Claims, 2 Drawing Sheets

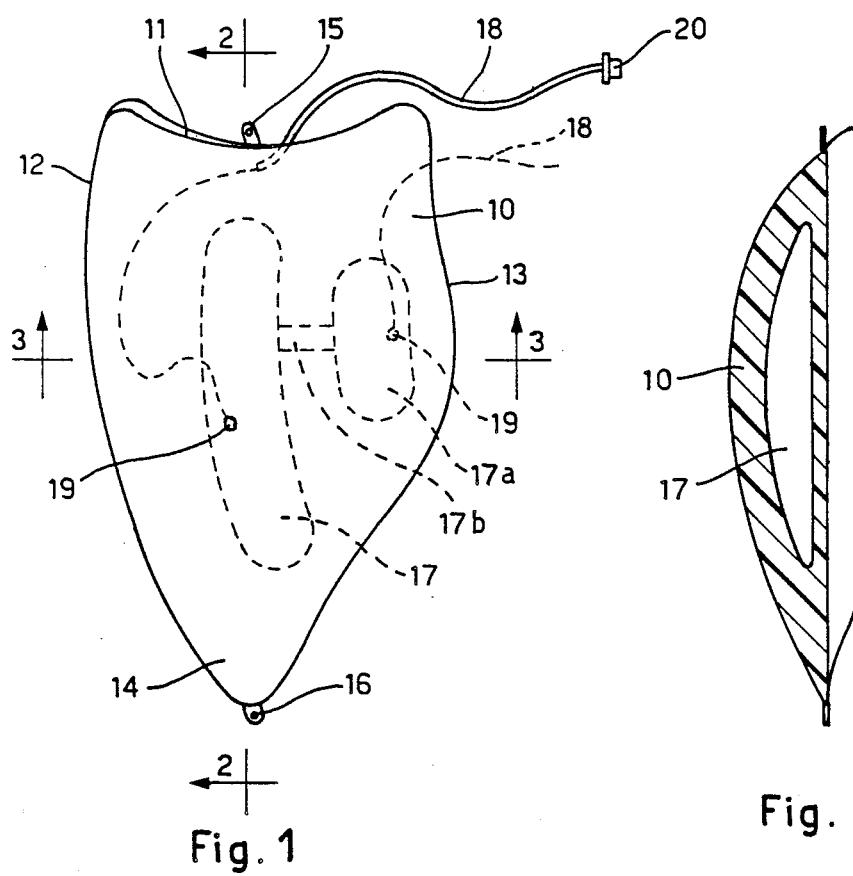
Fig. 1
Fig. 2
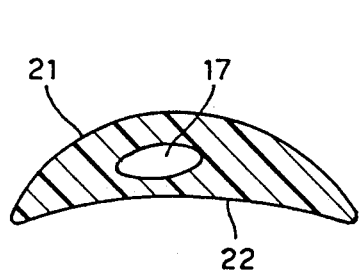
Fig. 3
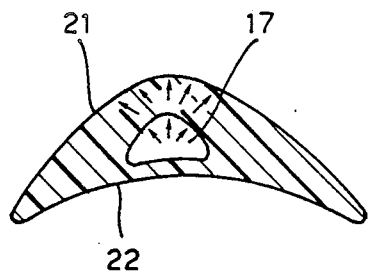
Fig. 4

EXPANDABLE PROSTHESIS FOR CORRECTING MYODYSTROPHIES

BACKGROUND OF THE INVENTION

This invention refers to an expandable prosthesis which can be used for the correction of myodystrophies, particularly those of the limbs, for example, to correct various types of hollows and depressions, or any localized malformation which requires the addition of material to give the relevant limb or part of the body the desired ideal shape.

At present there are limited possibilities of correcting malformations or myodystrophies due to deficiencies or localized thinness; the solution generally adopted is an autotransplant of subcutaneous fat, for example, to give a leg back its ideal shape.

However, this technique has limits due to both the scarcity of fat to transplant in each subject, which prohibits making up large losses of adipose and/or muscle tissue, and to the meagre consistency of the transplanted fat, which is poorly suited to replacing bands of more consistent muscle in a leg to be corrected.

The insertion of simple prostheses inside suitably constructed pockets in the limb to be corrected is not always able to supply the corrective shape necessary for the limb, since the volume and shape of a prothesis cannot be modified, and is unlikely to adapt to the generality or majority of cases.

Thus the object of the present invention is to provide a prosthesis for the correction of malformations or myodystrophies whose volume and shape can be modified after its insertion in an appropriate pocket made in the part of the body involved, giving the latter a localized shape and consistency suited to the area to be corrected.

SUMMARY OF THE INVENTION

The above can be obtained with a prosthesis according to the present invention, comprising a shaped body, in elastomeric material, e.g. silicon, having the shape and consistency of the part of the body to be corrected, said body of the prosthesis having at least one elastically dilatable part comprising a cavity in the form of an internal chamber which can be expanded by filling with pressurized liquid, which can be hypotonic, isotonic or hypertonic as required, and a filling tube connected to the above-mentioned cavity by means of a check valve.

The filling tube is preferably connected to the check valve in such a way as to be removable after filling, and the prosthesis itself can be fitted with parts to connect or anchor it to the limb in the area to be corrected.

The prosthesis can be of any shape and size, according to the area of the body involved, and each prosthesis can be provided with one or more expandable chambers stretching across and/or along at least part of the prosthesis itself.

BRIEF DESCRIPTION OF THE DRAWINGS

These and other characteristics of the expandable prosthesis according to the present invention will be evident in the description below, with reference to the attached drawings in which:

FIG. 1 is a front view of a prosthesis according to the invention;

FIG. 2 is a longitudinal section along line 2—2 of FIG. 1, before expansion;

FIG. 3 is a transverse section along line 3—3 of FIG. 1, before expansion;

FIG. 4 is a section similar to that in FIG. 3, after expansion caused by the filling of the internal chamber;

DESCRIPTION OF THE INVENTION

Figure 5:
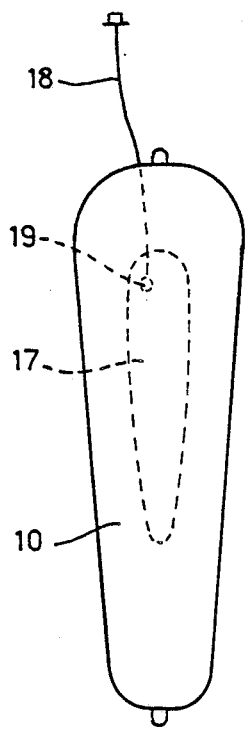
FIGS. 5, 6 and 7 show other possible shapes for a prosthesis according to this invention.

With reference to FIGS. 1 to 4, the prosthesis according to this invention will be described, particularly for correction of the lower limbs. The prosthesis comprising a substantially solid shaped body 10 formed of a silicon-based elastomer material, for example, whose consistency is such as to reproduce that of the limb muscular part to be corrected. In particular, the example in FIG. 1 shows the front view of a prosthesis for corrections in the calf region. As shown, the prosthesis is dimensioned and shaped to conform to a cavity or hollow in a lower limb of a patient. The prosthesis presents an arch shaped profile and a shape delimited by a concave upper side 11 to be attached below the knee, from which it extends down with an arch shaped side 12 towards the tibial region, and with a side 13 protruding into the calf region, to terminate with a rounded point in the lower part 14.

In an intermediate position on the upper concave side 11 the prosthesis has a fastening protrusion 15, and a fastening eyelet 16 or other equivalent means in correspondence with lower part 14.

Body 10 of the prosthesis is thick enough to allow the formation of at least one cavity or internal chamber 17 in correspondence with the expandable or dilatable zone or zones needed to give the prosthesis the desired volume and shape. As seen in the front view of FIG. 1, the size of the inner chamber 17 is substantially less than that of the entire front surface of the prosthesis. The internal chamber or cavity 17 extends with a constant or variable width for at least part of the central region of the prosthesis, and is destined to be filled with a fluid supplied at a certain pressure to chamber 17 through a filling tube 18 after the prosthesis itself has been placed in a pocket located under the band of muscle or submuscle in correspondence with the area of the limb or of the body to be corrected. Filling tube 18 is connected to chamber 17 of the prosthesis in a removable way through check valve 19 which is on the bottom wall and impedes the exit of filling liquid. The outer end of filling tube 18 terminates with a syringe valve 20 destined to be punctured at the time chamber 17 is filled.

In the case shown, the normal shape before filling is as in FIG. 3, in which front and rear prosthesis surfaces 21 and 22 have essentially constant radii of curvature or with little variation from one side of the prosthesis to the other to adapt to the shape of the limb to be corrected.

FIG. 4, instead, shows the shape which the same prosthesis assumes after chamber 17 has been filled with a suitable quantity of hypotonic, isotonic or hypertonic liquid at a relatively low pressure, sufficient to cause the prosthesis to expand frontally, increasing its volume by the desired amount to cause the limb to assume the shape desired. In fact, the arrows in FIG. 4 show the force exerted by the liquid injected into chamber 17 on the walls of the chamber, and thus on the front part of the prosthesis, deforming and arching it more in the central part. Chamber 17 is preferably delimited by a front wall which is thicker than the back contact wall.

In the case in FIGS. 1 to 4 a particular type of prosthesis with a single expansion chamber of constant width, stretching partially into the central region of the prosthesis between the upper concave side 11 and the pointed lower part 14 has been considered.

However, it is evident that the shape of the prosthesis could differ from that shown, and that chamber 17 could have a different shape, and that a single prosthesis could have one or more dilatable chambers 17, 17a in correspondence with the area or areas to expand. The chambers could also be interconnected by a conduit 17b or each may have its own filling tube 18 and its own filling valve 19.

Figure 6:
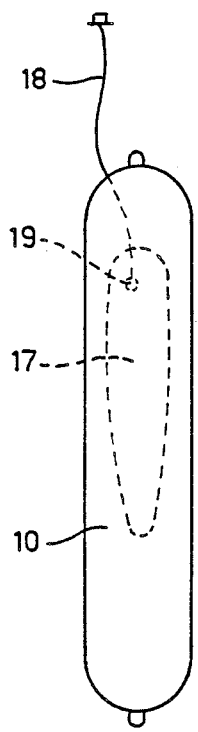
Figure 7:
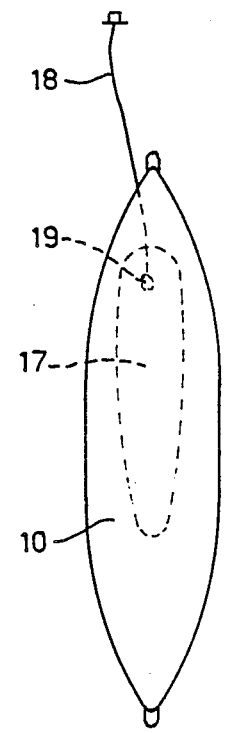

By way of example of the invention, and without restrictive force, FIGS. 5, 6 and 7, show other shapes of prostheses which could be used, for example, to make less voluminous corrections than in the previous case. In this case, too, the prostheses are obtained using silicon elastomer of a consistency similar to that of the missing muscle tissue and contain a single central cavity 17 extending through the prothesis in a shape similar to that of the prothesis itself. In both this and the preceding cases the front wall of the prosthesis, corresponding to cavity 17, is preferably thicker than the rear wall, e.g. double thickness, as shown.

From the above comments and the attached drawings, it will therefore be clear that there is provided an expandable prosthesis for the correction of myodystrophies or malformations, or rather, to fill cavities or hollows in the lower limbs or in other parts of the body, characterised by the presence of at least one inner chamber which can be filled with a fluid substance, atoxic, like the prosthesis itself, enabling even conspicuously apparent aesthetic defects to be corrected, thanks to the possibility of varying and increasing the volume of the prosthesis so as to assume the ideal shape desired.

The comments and illustrations should be understood to have been provided purely to exemplify the innovative principal for an expandable prosthesis of variable volume, as claimed.

What is claimed is:

1. A prosthesis for correction of myodystrophies of an area of a patient's limb, comprising, an outer body being substantially solid and being so dimensioned and shaped to conform to said area of the limb to be corrected, said outer body having a bottom surface and an outwardly extensible front surface, and at least one expandable inner chamber inside said outer body, said inner chamber being positioned nearer to said bottom surface than to said front surface, said outer body being formed of a silicon-based elastomer material having a consistency corresponding to that of the tissues of the area of the limb to be corrected; and a check valve for said expandable chamber, said check valve being positioned on said bottom surface, and tube means for feeding a liquid into said inner chamber to expand said inner chamber, said tube means being removably connected to said check valve.

2. A prosthesis according to claim 1 wherein the silicon-based elastomer forms front and rear walls of the inner chamber, said front wall having a greater thickness than said rear wall.

3. A prosthesis according to claim 2 wherein, in a front view, the inner chamber has a size which is substantially less than that of said front surface so that liquid in said inner chamber produces greater arching in those portions of the front surface that lie in front of said inner chamber.

4. A prosthesis according to claim 2 in which said inner chamber is an elongated chamber.

5. A prosthesis according to claim 1 having upper and lower ends which are provided with anchoring means.

6. A prosthesis according to claim 1 wherein the inner chamber is an elongated chamber which extends centrally and longitudinally of the prosthesis.

7. A prosthesis according to claim 1 having at least two said expandable inner chambers.

8. A prosthesis according to claim 7 wherein said inner chambers are connected to each other.

9. A prosthesis according to claim 7 wherein said inner chambers each have an independent check valve and tube means.

10. A prosthesis according to claim 1, wherein said inner chamber contains said liquid.

11. A prosthesis for correction of myodystrophies of an area of a patient's limb, comprising, an outer body being substantially solid and being so dimensioned and shaped to conform to said area of the limb to be corrected, said outer body having a bottom surface and an outwardly extensible front surface, and at least one expandable inner chamber inside said outer body, said inner chamber being positioned nearer to said bottom surface than to said front surface, said outer body being formed of a silicon-based elastomer material having a consistency corresponding to that of the tissues of the area of the limb to be corrected; said silicon-based elastomer forming front and rear walls of the inner chamber, said front wall of silicon-based elastomer having a greater thickness than said rear wall of silicon-based elastomer, and a check valve for said expandable chamber, said check valve being positioned on said bottom surface, and tube means for feeding a liquid into said inner chamber to expand said inner chamber, said tube means being removably connected to said check valve and a liquid in said inner chamber to outwardly deform said front wall and front surface.

12. A prosthesis according to claim 11 wherein, in a front view, the inner chamber has a size which is substantially less than that of said front surface so that pressurized liquid in said inner chamber produces greater arching in those portions of the front surface that lie in front of said inner chamber.

* * * * *